US006902521B2

(12) United States Patent
Baugh

(10) Patent No.: US 6,902,521 B2
(45) Date of Patent: Jun. 7, 2005

(54) SYSTEM AND METHOD TO ENHANCE GROWTH AND BIOLOGICAL FUNCTION OF LIVING SYSTEMS WITH PULSED ELECTROMAGNETIC ENERGY

(76) Inventor: Carl E. Baugh, Creation Evidenced Museum, 3102 FM 205, P.O. Box 309, Glen Rose, TX (US) 76043

( * ) Notice: Subject to any disclaimer, the term of this patent is extended or adjusted under 35 U.S.C. 154(b) by 106 days.

(21) Appl. No.: 10/114,656

(22) Filed: Apr. 2, 2002

(65) Prior Publication Data

US 2004/0102673 A1 May 27, 2004

Related U.S. Application Data

(60) Provisional application No. 60/281,203, filed on Apr. 3, 2001.

(51) Int. Cl.[7] ............................. A61B 17/52; A61N 2/00
(52) U.S. Cl. ......................................................... 600/9
(58) Field of Search .................. 600/9–15; 128/897.88; 405/128.85, 131, 130

(56) References Cited

U.S. PATENT DOCUMENTS

| 1,841,509 | A | * | 1/1932 | Van Damme ................. 47/19.2 |
|---|---|---|---|---|
| 3,557,753 | A | * | 1/1971 | Dantoni ....................... 119/260 |
| 3,658,051 | A | | 4/1972 | MacLean |
| 3,678,337 | A | | 7/1972 | Grauvogel |
| 3,890,486 | A | * | 6/1975 | Fitzgerald .................... 219/523 |
| 4,493,480 | A | * | 1/1985 | Nichol .......................... 256/10 |
| 4,825,588 | A | * | 5/1989 | Norman ....................... 47/66.1 |
| 5,014,699 | A | | 5/1991 | Pollack et al. |
| 5,087,353 | A | * | 2/1992 | Todd et al. .................... 210/94 |
| 5,192,874 | A | * | 3/1993 | Adams ......................... 307/125 |
| 5,195,940 | A | | 3/1993 | Baylink |
| 5,224,922 | A | | 7/1993 | Kurtz |
| 5,277,692 | A | | 1/1994 | Ardizzone |
| 5,304,111 | A | | 4/1994 | Mitsuno et al. |
| 5,338,286 | A | | 8/1994 | Abbott et al. |
| 5,480,373 | A | * | 1/1996 | Fischer et al. ................. 600/14 |
| 5,576,694 | A | * | 11/1996 | Touchton et al. ......... 340/573.3 |
| 5,595,564 | A | * | 1/1997 | Pinna ........................... 600/14 |
| 5,741,317 | A | * | 4/1998 | Ostrow ......................... 607/85 |
| 5,935,516 | A | | 8/1999 | Baugh |
| 6,004,257 | A | * | 12/1999 | Jacobson ....................... 600/9 |
| 6,203,486 | B1 | * | 3/2001 | Miller et al. .................... 600/9 |
| 6,398,455 | B1 | * | 6/2002 | V.o slashed.lstad .......... 405/43 |
| 6,519,131 | B1 | * | 2/2003 | Beck ............................ 361/232 |
| 2003/0056432 | A1 | * | 3/2003 | Prevost .................... 47/1.01 F |

OTHER PUBLICATIONS

Namba, K. et al (1995) "Effect of Magnetic Field on Germination and Plant Growth." Acta Horticulturae, 399, 143–147.

Matsuda, T. et al (1993) "Influences of Magnetic Fields on Growth and Fruit Production of Strawberry," Acta Horticulturae, 348, p. 378–380.

Ginzo, H.D. and Decima, E.E. (1995) "Weak Static Magnetic Fields Increase the Speed of Circumnutatioin in Cucumber Tendris," Experientia, 51, p. 1090–1094.

Baker, R.R. (1980) "Goal Orientation by Blindfolded Humans After Long–Distance Displacement: Possible Involvement of a Magnetic Sense," Science, 210, p. 555–557.

* cited by examiner

Primary Examiner—Samuel G. Gilbert
(74) Attorney, Agent, or Firm—Hahn Loeser & Parks LLP; David J. Muzilla, Patent Agent

(57) ABSTRACT

The present invention is a system and method of enhancing growth and biological functions of living systems through application of pulsed electromagnetic energy. Electrical wiring is placed below the surface of a selected area such as a garden, athletic playing surface, livestock pen, or golf course for emission of electromagnetic energy to plants and animals, including humans. The electric wiring is connected to a electromagnetic generator which generates and controls the electromagnetic energy being applied. The electric wiring is placed below the surface of the selected area at a depth between 1 and 30 inches. The electromagnetic energy has a magnetic field component in the range of 0.5 to 30 Gauss, and the frequency range of the pulses between 0.5 and 30 Hertz.

11 Claims, 5 Drawing Sheets

SYSTEM AND METHOD TO ENHANCE GROWTH AND BIOLOGICAL FUNCTION OF LIVING SYSTEMS WITH PULSED ELECTROMAGNETIC ENERGY

This application claims the benefit of U.S. Provisional Application No. 60/281,203 filed Apr. 3, 2001.

FIELD OF THE INVENTION

The present invention is generally a means to enhance growth and performance of biological systems. More specifically, the present invention is a system and method to enhance physiological performance of organisms through application of pulsed electromagnetic energy.

BACKGROUND OF THE INVENTION

Use of electromagnetic energy to increase physiological performance of organisms has long been attempted. However, many of these techniques have been limited to belts, pads or mats which apply magnetic or electromagnetic energy to the person or other organism. Problems inherent in these techniques include the necessity for the organism to wear the belt or pad, and the necessity for a portable power source in order to generate electromagnetic energy. Furthermore, these techniques do not effect the environment surrounding the organism, nor do they bring the environment and organism into gentle resonance. Accordingly, there is a demand for an apparatus and method of applying pulsed electromagnetic energy to an organism and its surrounding environment that is without the aforementioned disadvantages.

SUMMARY OF THE INVENTION

The present invention is an apparatus and method of applying pulsed electromagnetic energy to organisms such as humans or other animals, and to the organism's surrounding environment such as grass and other organisms within this environment. Specifically, electrical wiring which emits pulsed electromagnetic energy, is placed under the surface of the area in which the humans or other organisms are situated. This includes putting wiring in proximity to or under the surface of a variety of environments, such as livestock pens, poultry pens, ponds, garden plots, athletic courts, and golf courses. The system and method of the present invention is used in association with various different organisms or living systems such as humans and other animals, as well as plants, for example.

Electromagnetic energy is then pulsed through the electric wiring and diffused throughout the area surrounding the wiring, including the atmosphere above the surface of the selected area. As the electromagnetic energy diffuses, it is applied to both the plants and animals within the selected area. The application of the pulsed electromagnetic energy brings these organisms into gentle resonance and enhances biological function and genetic expression of these organisms. Generally, better health, increased appetite and higher consumption of water, are among the positive effects that have been experienced by participating humans.

DETAILED DESCRIPTION OF THE PREFERRED EMBODIMENT

Reference will now be made in detail to the present preferred embodiments of the present invention, examples of which are illustrated in the accompanying drawings. Whenever possible, the same reference numbers will be used throughout the drawings to refer to the same or like parts.

Figure 1:
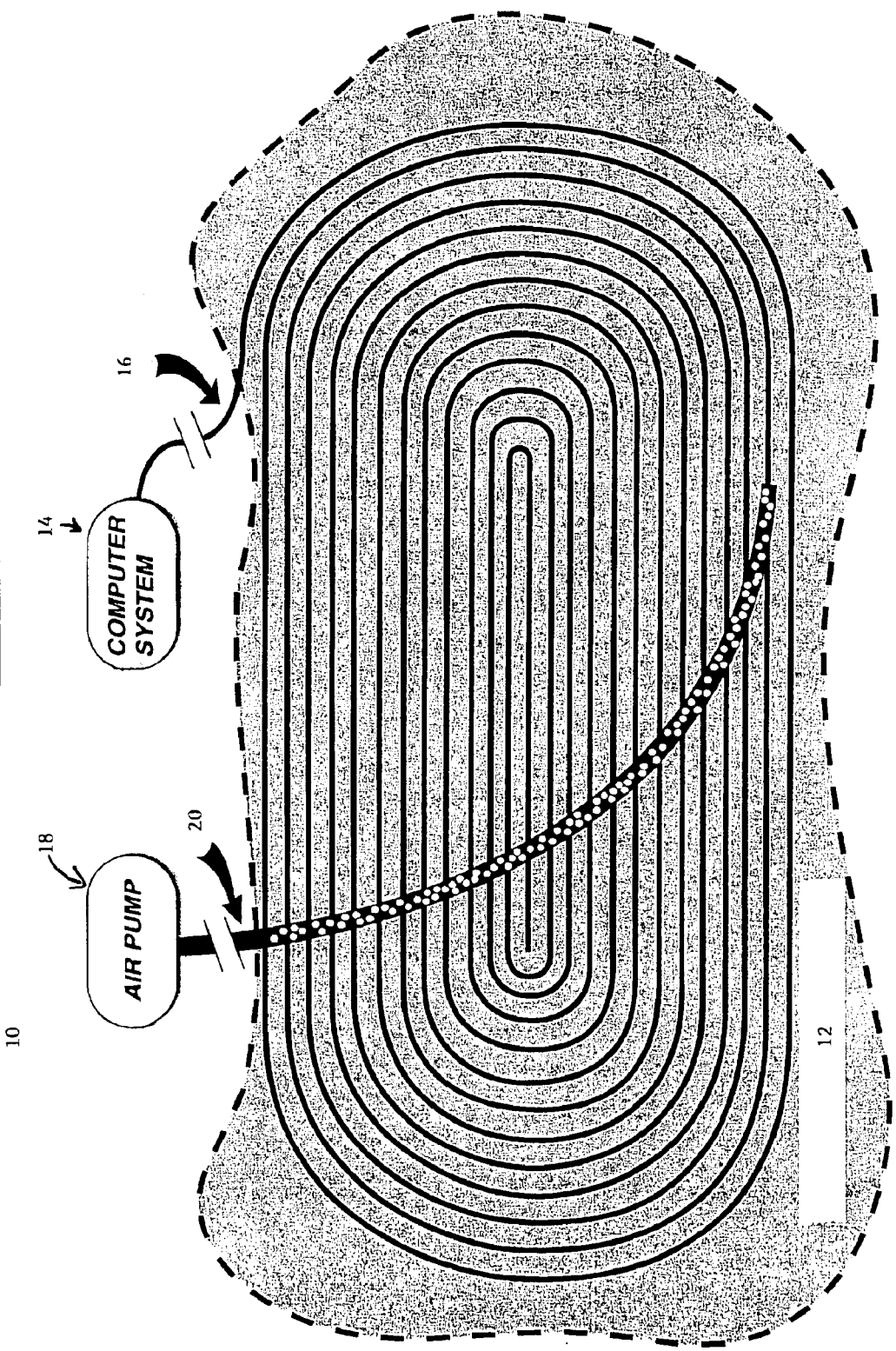
FIG. 1 is a schematic diagram of a first preferred embodiment of the present invention, illustrating the application of pulsed electromagnetic energy to an aquatic bio-system.

Shown in FIG. 1 is a first preferred embodiment of the present invention. It illustrates the application of pulsed electromagnetic energy to any aquatic setting. Shown generally at 10, this embodiment includes a water reservoir 12, such as an aquarium, pool, pond or other body of water. Below water reservoir 12 is placed electric wiring 16. Although in FIG. 1 electric wiring 16 is shown in a continuous open ended coil of wiring, electric wiring 16 can be positioned in a discontinuous fashion having a main line and a plurality of other lines extending from the main line. The electrical wiring 16 is placed over a substantial area of water reservoir 12, from 1 to 30 inches below the bottom surface of the water reservoir 12 and is insulated from the surrounding elements and cross currents from other cables. If water reservoir 12 has sides, such as in a pool, electric wiring 16 can also be placed behind the surface of the sides of reservoir 12. Electric wiring 16 is insulated by neutral materials, such as plastics, that will insulate electric wiring 16, yet not produce a charge in the surrounding soil or substance. Further, highly shielded electrical wire is not desired as it decreases the capacity of diffusion of the pulsed electromagnetic energy. The pulsed electromagnetic energy is supplied to electric wiring 16, and is controlled by an electromagnetic energy generator 14.

Optionally, an air pump 18 and perforated air hose 20 may be included in the system embodied in FIG. 1. Air pump 18 and air hose 20 provide an oxygen source to the water within reservoir 12, thus, aerating the water and increasing the oxygen concentration of the water.

In use, pulsed electromagnetic energy is applied to the electric wiring 16 by an electromagnetic energy generator 14. Various electronic components may be utilized to generate electromagnetic energy for use in this system, such as a computer system or a electromagnetic wave generator for example. Preferably, the electromagnetic energy has a magnetic field component in the range of 0.5 to 30 Gauss, and the frequency range of the pulses between 0.5 and 30 Hertz. Concurrently, air pump 18 pumps air through hose 20 to increase the oxygen concentration of the water. The water in free motion around the air bubbles is energized to a higher state because of the application of the pulsed electromagnetic energy, and thus becomes even more saturated with oxygen.

Application of the electromagnetic energy to reservoir 12 provides for application of electromagnetic energy to both plants and animals situated within the aquatic system. The affected plants and animals exhibit enhanced physiologic effects such as increased growth and overall health for example. Furthermore, the highly oxygenated and energized water can then be utilized for watering plants which are not directly exposed to electromagnetic energy.

Figure 2:
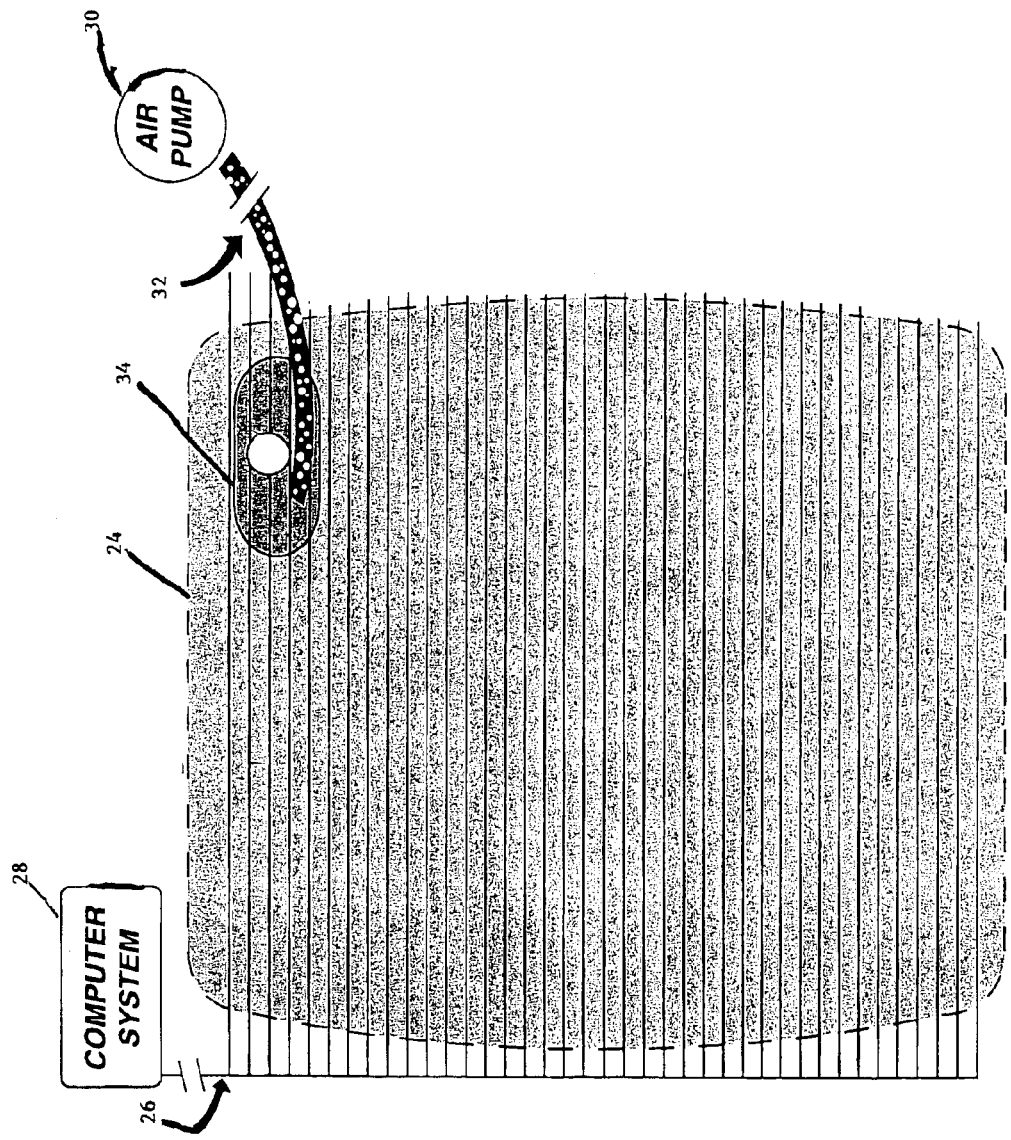
FIG. 2 is a schematic diagram of a second preferred embodiment of the present invention, illustrating the application of pulsed electromagnetic energy to livestock pens.

Referring now to FIG. 2, there is shown a second embodiment of the present invention, illustrating the application of pulsed electromagnetic energy to livestock animal pens. In this embodiment, there is a stock pen 24 which can be used to retain any type of livestock animal or poultry. Further, it should be understood that such a stock pen can be enclosed in buildings or open fields. Electrical wiring 26 extends below the surface and laterally across first stock pen 24 to cover at least a substantial area of stock pen 24. As in the first embodiment, electrical wiring 26 is comprised of electrical wiring having neutral insulating materials, and is placed under the surface of the selected area at a preferred depth of 1 to 30 inches. Electromagnetic energy generator 28 generates and transmits electromagnetic energy to electric wiring 26. Optionally, this system may also include a water tank 34 for watering of the animals. An air pump 30 may be utilized to pump air into the water tank 34 through hose 32. Aeration of water tank 34 by pump 30 increases the oxygen concentration of the water held within water tank 34.

If the stockyard is enclosed, the electric wiring is buried at a depth between 1 and 30 inches within the dirt or other flooring material, such as concrete, for example.

Figure 3:
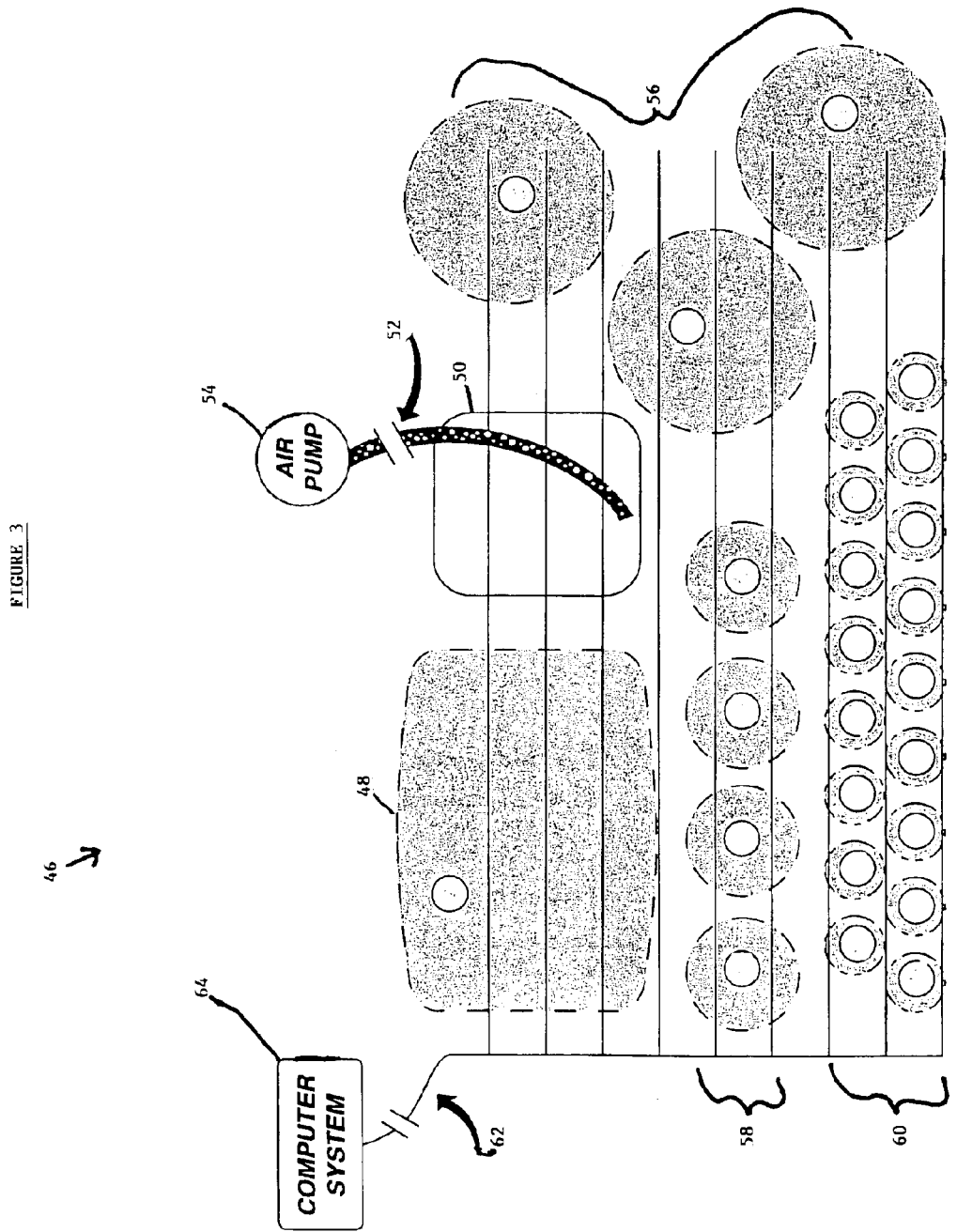
FIG. 3 is a schematic diagram of a third preferred embodiment of the present invention, illustrating the application of pulsed electromagnetic energy to a plant bio-system.

Now referring to FIG. 3, there is shown a third embodiment of the present invention illustrating the application of electromagnetic energy to a plant bio-system 46, such as a garden. The plant based bio-system may include, for example, a grain plot 48, fruit or other trees 56, plants 58 and/or flowers 60. The plants may either be grown within the ground itself or within planting containers such as pots and the like. The system 46 may optionally also include a water reservoir 50, which is aerated by hose 52 and air pump 54 to increase the oxygen concentration of the water held within reservoir 50. Electromagnetic energy is generated by an electromagnetic energy generator 64 and applied to system 46 via electric wiring 62. Electric wiring 62 is position to cover at least a substantial portion of system 46, and is placed below the surface of system 46, at a depth of 1 to 30 inches. The plants affected by the application of the electromagnetic energy exhibit improved physiological effects such as improved and more rapid growth, and better overall health for example.

Figure 4:
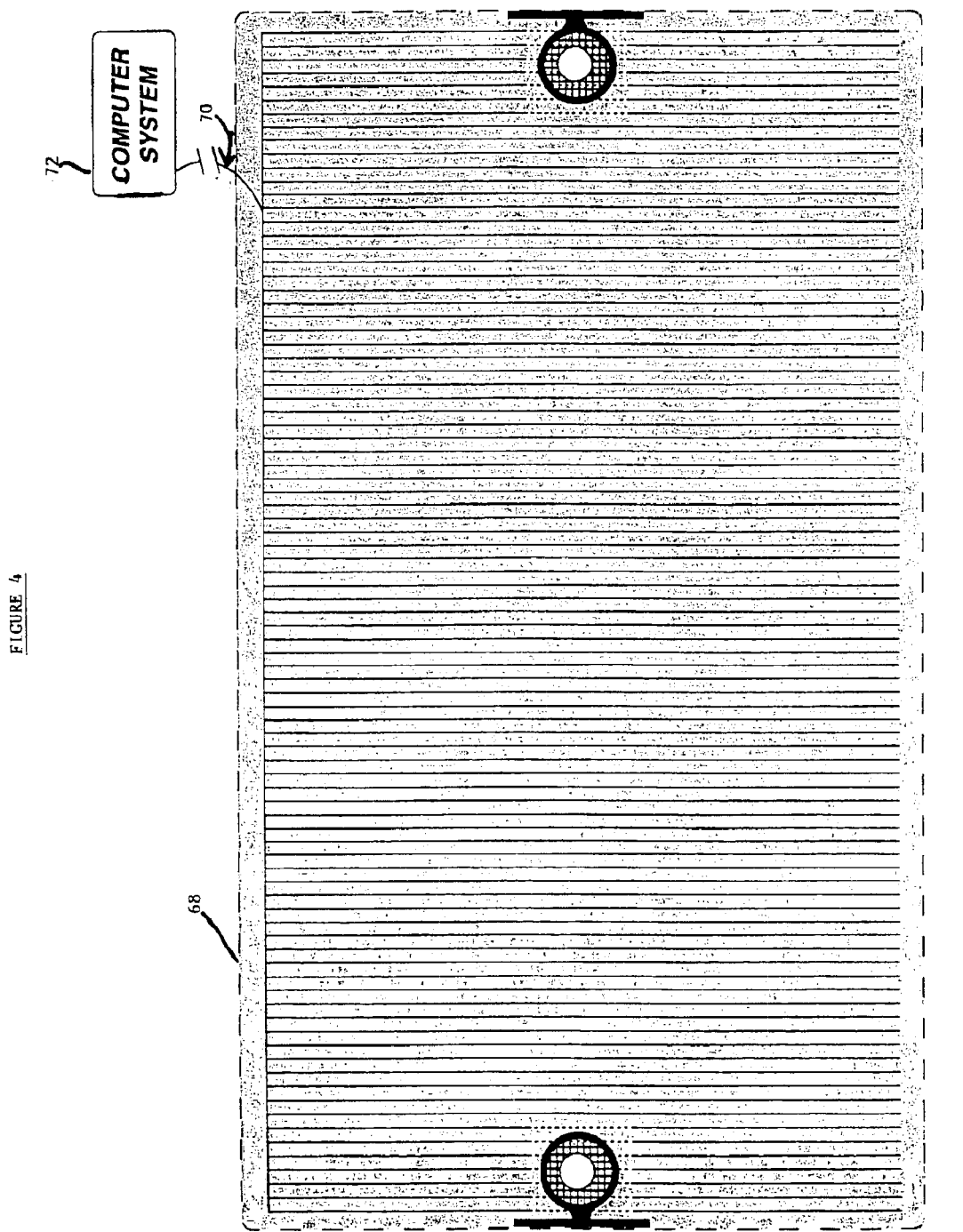
FIG. 4 is a schematic diagram of a fourth preferred embodiment of the present invention, illustrating the application of pulsed electromagnetic energy to a basketball court.

Shown in FIG. 4 is yet another embodiment of the present invention, illustrating applying electromagnetic energy to an athletic playing surface 68, such as, for example a basketball court, a football field, a soccer field, a swimming pool, playgrounds or other playing surfaces. Electrical wiring 70 is placed below playing surface 68 at a preferred depth of between 1 and 30 inches. Electromagnetic energy generator 72 generates and conducts electromagnetic energy through electric wiring 70 to diffuse the electromagnetic energy throughout playing surface 68. The electromagnetic energy is applied to those persons playing or competing on playing surface 68. Upon application of the electromagnetic energy, humans experience higher energy levels for longer periods of time, reduced fatigue, less muscle strain and soreness, in addition to increased concentration and precision in playing the particular sport.

Figure 5:
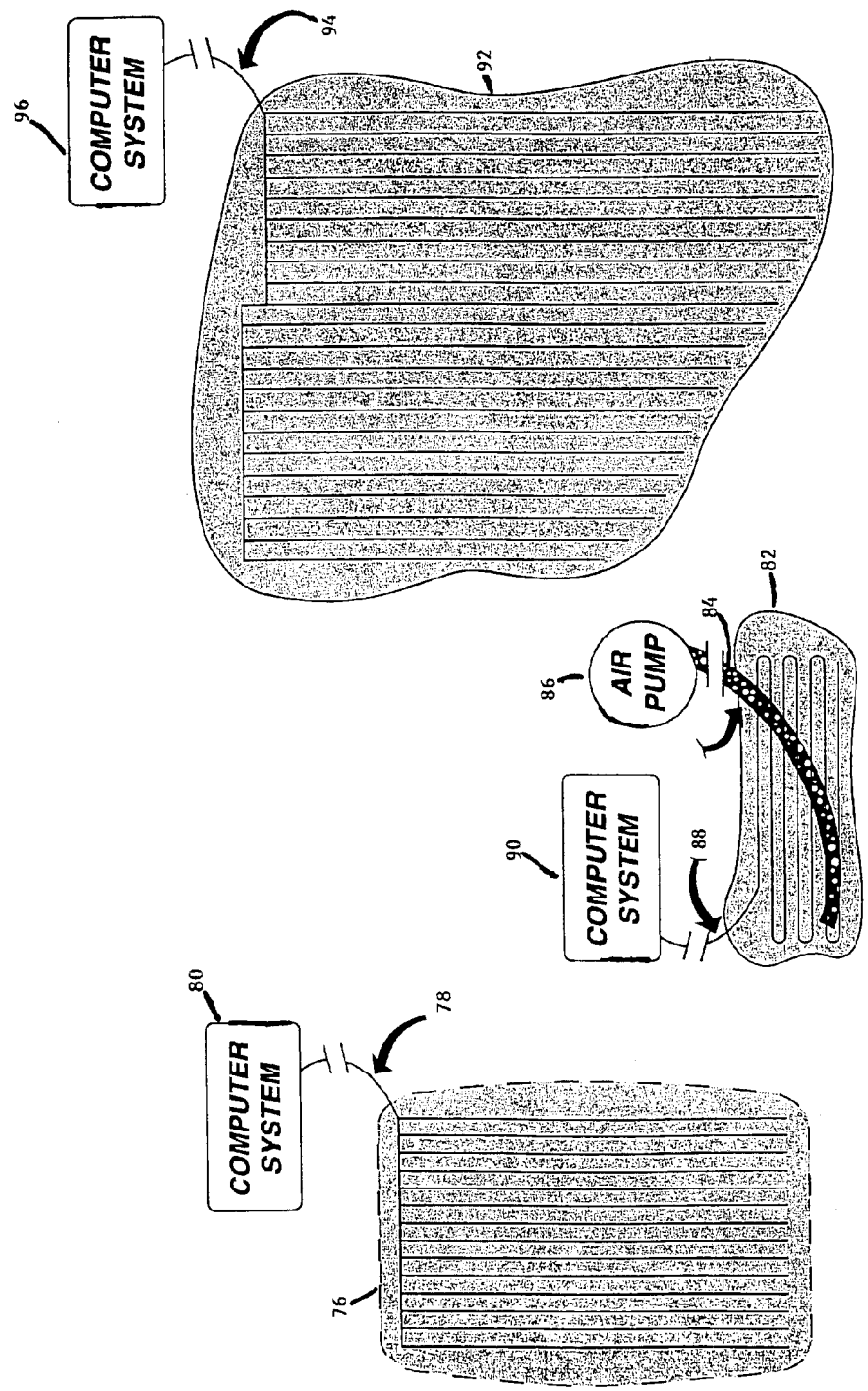
FIG. 5 is a schematic diagram of a fifth preferred embodiment of the present invention, illustrating the application of pulsed electromagnetic energy to a golf course.

Referring now to FIG. 5, there is shown yet another embodiment of the present invention, illustrating application of electromagnetic energy to a golf course hole. This embodiment includes a tee box 76, a green 92 and/or optionally a water reservoir 82. Below tee box 76 is placed electrical wiring 78, which is placed at a depth of 1 to 30 inches. Electrical wiring 94 is also placed below golf green 92 at a preferred depth of 1 to 30 inches. If water reservoir 82 is utilized, electrical wiring 88 is positioned below the bottom of reservoir 82 at a depth of 1 to 30 inches for emission of electromagnetic energy. Treated water from reservoir 82 may be used to water the golf course fairways, greens, or other plants associated with the course as to achieve the benefits as described above in relation to the plant based bio-system embodiment. Electromagnetic energy generators 80, 90 and 96 produce and emit electromagnetic energy through electrical wiring 78, 88 and 94 respectively. Optionally, a single electromagnetic generator can control the emission of electromagnetic energy through electrical wiring 78, 88 and 94. As with the above described embodiments, electromagnetic energy generators 80, 90 and 96 emit electromagnetic energy having a magnetic field component in the range of 0.5 to 30 Gauss, and the frequency range of the pulses between 0.5 and 30 Hertz.

Effects seen through application of the electromagnetic energy to a grass surfaces such as soccer fields, play grounds, football fields, golf greens and tee boxes include more rapid and healthier growth of grass, faster regeneration or repair of divots and ball marks, fewer attacks to these grasses by pests as the grasses are healthier. The human players experience gentle invigoration, increased energy, greater concentration, and less muscle soreness or strain. Increased mental activity and faster healing of wounds has also been noted.

Sporting equipment such as golf clubs are not affected by the application of electromagnetic energy because no sustained electrical current is conducted to the metal portions of the clubs.

In use with any of the above embodiments, the characteristics of the electromagnetic energy remain the same, that is electromagnetic energy having a magnetic field component in the range of 0.5 to 30 Gauss, and the frequency range of the pulses between 0.5 and 30 Hertz. The cycling/hertz of the electromagnetic energy is varied slowly during a 24 hour period. In application of pulsed electromagnetic energy to humans, the magnetic field strength is adjusted to be within 4 to 8 Gauss. The placement of the electrical wiring below the surface of the selected area is adjusted to accommodate these parameters. Further, it is important to note that the spacing of the electric wiring in the above described embodiments may be altered to achieve desired effects.

Although the principles, preferred embodiments and preferred operation of the present invention have been described in detail herein, this is not to be construed as being limited to the particular illustrative forms disclosed. They will thus become apparent to those skilled in the art that various modifications of the preferred embodiments herein can be made without departing from the spirit or scope of the invention as defined by the appended claims.

What is claimed:

1. A method of enhancing the growth and biological function of living systems, said method comprising:

generating electromagnetic energy having a magnetic energy component in the range of 0.5 to 30 Gauss;

dispersing said electromagnetic energy through a length of electric wiring in order to affect said living systems; and aerating a body of water associated with an environment of said living systems for the purpose of increasing an oxygen content of said body of water.

2. An apparatus for enhancing biological function of living systems within an environment, said apparatus comprising:

an electromagnetic energy generator to generate pulsed electromagnetic energy having a magnetic energy component in the range of 0.5 to 30 Gauss and a pulse frequency range between 0.5 and 30 Hertz;

at least one length of electric wire coupled to said electromagnetic energy generator such that said at least one length of electric wire emits said pulsed electromagnetic energy into said environment at an intensity and a frequency to affect a positive response of said biological function of said living systems;

an air pump; and an air hose, wherein said air pump and said air hose are used to aerate a body of water within said environment for the purpose of increasing an oxygen content of said body of water.

3. The apparatus of claim 2, wherein said length of electric wire is positioned at a depth between 1.0 and 30 inches below a surface of said environment.

4. The apparatus of claim 2, wherein said at least one length of electric wire comprises at least two lengths of wire configured as an open ended loop configuration.

5. The apparatus of claim 2, wherein said at least one length of electric wire is configured with at least one main line and a plurality of lines extending from said at least one main line.

6. The apparatus of claim 2, wherein said environment is selected from the group consisting of livestock yards, gardens, orchards, athletic grounds, and play grounds.

7. The apparatus of claim 2, wherein said environment is selected from the group consisting of ponds, lakes, swimming pools, and aquariums.

8. The apparatus of claim 2, wherein said at least one length of electric wire is insulated by a non-conductive material.

9. The apparatus of claim 2, wherein said electromagnetic energy generator comprises a computer-based system.

10. An apparatus for enhancing biological function of living systems within an environment, said apparatus comprising:

an electromagnetic energy generator to generate electromagnetic energy;

at least one length of electric wire coupled to said electromagnetic energy generator such that said at least one length of electric wire emits said electromagnetic energy into said environment at a magnetic component intensity in the range of 0.5 to 30 Gauss and a pulse frequency range between 0.5 and 30 Hertz to affect a positive response of said biological function of said living systems;

an air pump; and an air hose, wherein said air pump and said air hose are used to aerate a body of water within said environment for the purpose of increasing an oxygen content of said body of water.

11. A method of enhancing the growth and biological function of living systems, said method comprising:

aerating a body of water associated with an environment of said living systems for the purpose of increasing an oxygen content of said body of water;

generating electromagnetic energy;

emitting said electromagnetic energy into said environment of said living systems from at least one open ended length of electric wiring positioned at least beneath said body of water.

* * * * *